United States Patent
Kirsch

(10) Patent No.: US 8,696,626 B2
(45) Date of Patent: Apr. 15, 2014

(54) DEBUBBLER

(76) Inventor: Claudia F. E. Kirsch, Los Angeles, CA (US)

( * ) Notice: Subject to any disclaimer, the term of this patent is extended or adjusted under 35 U.S.C. 154(b) by 332 days.

(21) Appl. No.: 12/182,489

(22) Filed: Jul. 30, 2008

(65) Prior Publication Data

US 2010/0030151 A1 Feb. 4, 2010

(51) Int. Cl.
*A61M 1/00* (2006.01)
*B01D 19/00* (2006.01)
*B01D 59/26* (2006.01)

(52) U.S. Cl.
USPC ............... 604/126; 604/122; 96/193; 95/46; 422/48

(58) Field of Classification Search
USPC ............ 604/122, 123, 126, 128, 129; 96/193; 95/46; 422/48
See application file for complete search history.

(56) References Cited

U.S. PATENT DOCUMENTS

| | | | | |
|---|---|---|---|---|
| 4,624,658 | A | * | 11/1986 | Mardorf et al. ............. 604/121 |
| 4,636,313 | A | | 1/1987 | Vaillancourt |
| 4,941,897 | A | * | 7/1990 | Vann, III ........................ 96/8 |
| 5,055,198 | A | * | 10/1991 | Shettigar ..................... 210/650 |
| 6,503,225 | B1 | * | 1/2003 | Kirsch et al. ................. 604/126 |
| 7,097,690 | B2 | * | 8/2006 | Usher et al. .................... 95/46 |
| 7,959,715 | B2 | * | 6/2011 | Kavazov et al. .................. 96/6 |
| 2002/0162455 | A1 | | 11/2002 | Bikson et al. |
| 2003/0207464 | A1 | * | 11/2003 | Lemmo et al. ................ 436/180 |
| 2004/0057854 | A1 | * | 3/2004 | Wakabayashi et al. ........ 417/448 |
| 2005/0077225 | A1 | | 4/2005 | Usher et al. |
| 2006/0163140 | A1 | | 7/2006 | Taylor et al. |
| 2007/0278145 | A1 | | 12/2007 | Taylor et al. |
| 2008/0269687 | A1 | * | 10/2008 | Chong et al. .................. 604/180 |

FOREIGN PATENT DOCUMENTS

| | | |
|---|---|---|
| JP | 05505540A A | 8/1993 |
| JP | 200-526098 A | 12/2001 |
| WO | WO9113677 A1 | 9/1991 |

OTHER PUBLICATIONS

Liqui-Cel Membrane Contractors—Gas Transfer Technology from www.liqui-cel.com.
Brochure, SuperPhobic Membrane Contactors, Membrana.
Brochure, Liqui-Cel Membrane Contactors, Membrana.
Office Action issued from Japanese Patent Office dated Jul. 30, 2013.

* cited by examiner

*Primary Examiner* — Nicholas Lucchesi
*Assistant Examiner* — Jenna Zhang
(74) *Attorney, Agent, or Firm* — Jeffrey G. Sheldon; Sheldon Mak & Anderson

(57) ABSTRACT

A device for removal of a gas from a liquid in a medical infusion line has a housing containing a plurality of hollow fiber membranes. Preferably liquid passes on the exterior of the membranes and gas bubbles in the liquid pass into the lumens of the hollow fiber membranes. This is for removal by a vacuum. The device can include its own vacuum chamber. When the device has its own vacuum chamber, it can include a warning system to alert a user to replace the device when the provided vacuum is no longer sufficient.

15 Claims, 1 Drawing Sheet

DEBUBBLER

BACKGROUND

Figure 1:
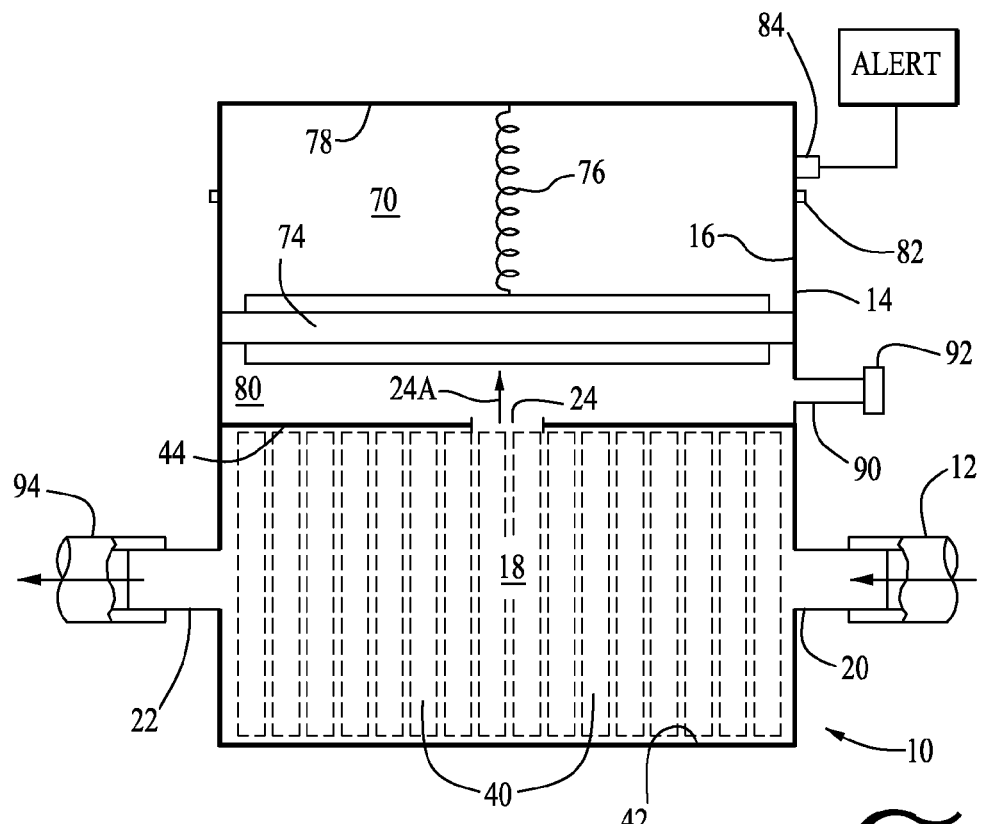

The present invention relates generally to a device for removal of gases from liquids, particularly liquids delivered to a patient during a medical procedure.

When introducing a liquid to a patient, to minimize the risk of injury to the patient from air embolism, it is generally necessary to eliminate air or other gases from the liquid delivery. My U.S. Pat. No. 6,503,225, which is incorporated herein by reference, is directed to a device that serves this purpose.

However, I determined that it is desirable to improve on this device. For example, it is desirable to reduce the pressure drop across the debubbler for improved efficiency. Also, my prior device requires an external vacuum. I have determined that in some applications an external vacuum is not readily available, particularly in third world countries. Accordingly, I determined there is a need for a more efficient device which also can provide its own vacuum.

SUMMARY

The present invention provides a device with these improvements. The device allows removal of gas, and particularly air bubbles, from a liquid in a medical fluid infusion line. The device comprises a housing having an internal chamber, an inlet port for receiving liquid from the medical fluid in fusion line for flow into the internal chamber, and an outlet port for discharging the liquid from the internal chamber, as well as a vacuum vent. There are a plurality of hollow fiber membranes in the chambers. The membranes have an internal lumen and are substantially impervious to the liquid, but are pervious to gas in the liquid. The internal lumens of the membranes are in gas flow communication with the vent port. Gas bubbles in the liquid flow into the lumens of the membranes, from which they are evacuated through the vent port.

In a preferred version of the invention, the device is self-contained with its own vacuum. In this version of the invention, the device comprises a housing having an internal surface, an internal degassing chamber, an inlet port for receiving liquid from the medical infusion line for flow into the degassing chamber, an outlet port for discharging a liquid from the degassing chamber, and a vent port in communication with the degassing chamber. There is a vacuum chamber housing in gas flow communication with the vacuum vent for withdrawing gas from the degassing chamber. In this version of the invention the liquid can flow either inside the lumens of the hollow membranes with gas passing to the exterior of the membranes, or optionally the liquid can flow on the outside of the membranes, like the first version, where the gas passes through the membrane walls into the lumens. For efficiency, the second option is preferred.

Preferably there is a piston movably mounted in the vacuum chamber for creating a vacuum in the vacuum chamber. Preferably the piston has a length about equal to the distance between the inlet port and the outlet port. There can be biasing means, such as a spring, for biasing the piston away from the vacuum port. Typically the vacuum at the vacuum vent is from about 25 torr to about 500 torr, and more preferably from about 50 to about 125 torr.

Preferably there is an indicator, such as a visible mark on the housing, for indicating when the piston has moved to a position indicating that it is time to replace or adjust the device. Instead of the indicator, or in addition to it, there can be a switch activatable by the piston for providing a perceptible alert, such as a flashing light, to replace or adjust the device. When both the indicator and the alert switch are provided, the alert switch is positioned so it is activated after the piston has moved by the indicator.

Optionally, the device that includes a built in vacuum source also can have a closable vacuum connection to the vacuum chamber for connecting the device to an external vacuum source when an external vacuum source is available.

In use of the device, the liquid is introduced into the inlet port of the device and gas in the liquid is automatically removed.

DRAWINGS

Figure 2:
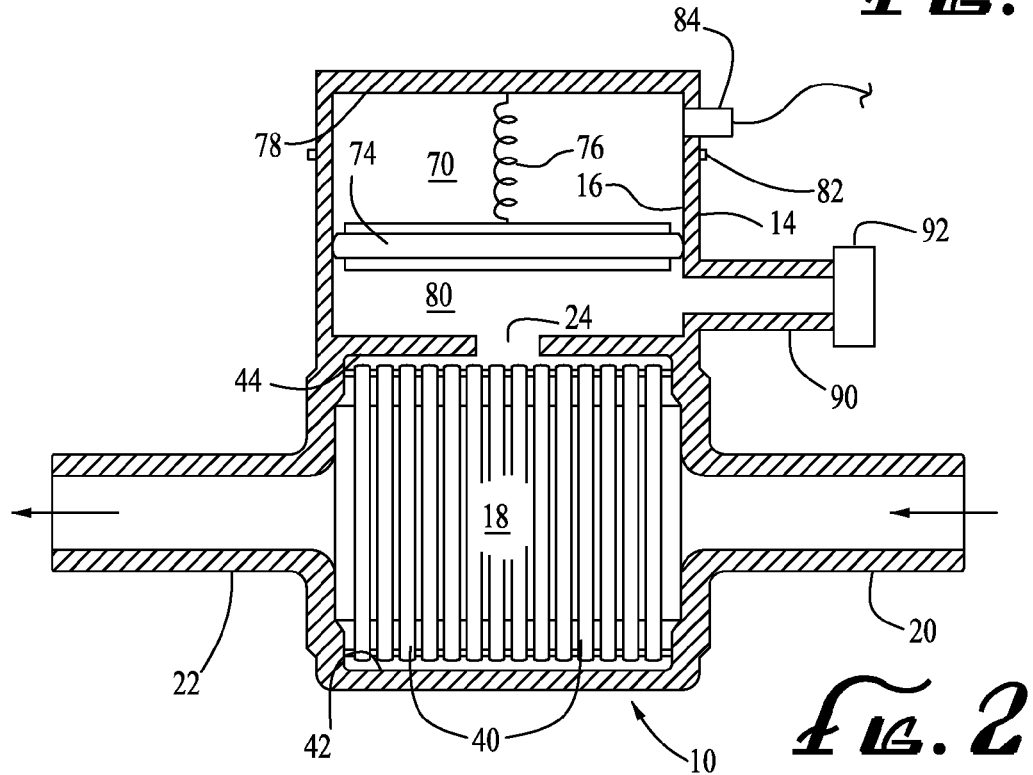

These and other features, aspects, and advantages of the present invention will become better understood with reference to the accompanying description, appended claims and accompanying drawings where:

FIG. 1 schematically presents a gas removal device having features of the present invention; and FIG. 2 is a partial sectional view of the device of FIG. 1.

DESCRIPTION

With reference to the figures, a device 10 for removal of gas from a liquid in a medical infusion line 12 comprises a housing 14 having an internal surface 16, an internal degassing chamber 18, also referred to as a debubbling chamber, an inlet port 20 in fluid communication with the infusion line 12, an outlet port 22 for discharging liquid from the degassing chamber 18, and a vent 24 in fluid communication with the degassing chamber.

The device 10 can be used for any liquid containing a gas, and particularly for intraarterial or intraarterial applications, including without limitation: conventional angiography, interventional angiography, neurointerventional angiography, cardiac catheterization, arterial pressure monitoring, Swanz-Ganz catheters, syringes or intravenous lines for injection of drugs or solutes or nutrients, arterial lines, venous lines, and indwelling catheters, or during operative procedures.

There are a plurality of hollow fiber membranes 40 in the debubbling chamber 18. The membranes 40 can be made of the same material and have the same configuration, with liquid flowing through the lumens of the fibers, as described in my aforementioned U.S. Pat. No. 6,503,225. However, it is preferred that the liquid flow on the exterior of the membranes with gas being transported through the walls of the fibers into an interior lumen. In this version of the invention, the membranes 40 extend generally transverse to the liquid flow, with the liquid flowing generally from the inlet port 20 to the outlet port 22.

The hollow fiber membranes 40 have an internal lumen and are substantially impervious to the liquid and are pervious to gas in the liquid. The internal lumens of the membranes are in gas flow communication with the vacuum port or vent 24 as shown by arrow 24A.

The hollow fiber membranes 40 extend generally transverse to the axis of the housing 20, from adjacent side wall 42 to an opposite side wall 44. Thus the longitudinal axis of the fibers are generally oriented at an angle of 90 degrees relative to the liquid flow through the degassing chamber. However the fibers can be at any angle relative to the liquid flow, including parallel. Also, not all fibers need to be oriented in the same direction nor need to be linear.

The fibers 40 can be a microporous hydrophobic hollow fiber membrane, such as are available commercially as polyolefin membranes. Example materials include: polypropylene, polyethylene, or polymethylpentene. The fibers 40 typically have an outside diameter of approximately 200-400 microns, a wall thickness of approximately 25-50 microns, a pore size of between approximately 0.01 to 0.2 microns (sufficiently small to prevent fluid breakthrough), and a porosity of approximately 10-50% (sufficiently high to provide adequate flux of gas and gas bubble passage from the aqueous fluid external to the lumens of the fibers 40 to the gas phase interior of the fibers 40). The fiber membranes 40 are constructed of suitable FDA grade materials. A porous hydrophobic membrane allows for direct removal of bubbles from aqueous fluid without liquid penetration into the pores according to the Young-Laplace formula. Removal of dissolved gasses present in the liquid can be additionally facilitated by use of vacuum on the lumen of the fibers, through the vacuum port or vent 24, due to partial pressure difference of the gasses in the liquid and gas phases according to Henry's Law.

Although microporous hydrophobic hollow fiber membranes are described above, any porous hollow fiber material, whether hydrophobic or hydrophilic, can be used to form the fibers 40, with the application of a thin coating or skin of a polymer having suitable permeability to the dissolved gasses (for example, oxygen, nitrogen, carbon dioxide) in the aqueous liquid passed through the tubing 12, but rendering the pores of the fibers 40 impermeable to passage of the aqueous liquid therethrough. Example polymer coatings include silicones, polymethylpentene, and other FDA grade polymers. The polymer skin is preferably applied to the liquid surface (the internal lumen surface) of the hollow fiber 40, to prevent liquid penetration into the pores. Vacuum applied to the lumen facilitates removal of dissolved gasses from the liquid.

The fiber membranes 40 can be held in place within the housing 20 by fluid tight seals. The seals can comprise, for example, a potting resin that fills the voids between the fibers 40, and bonds to the interior surface 16 of the housing 14 to form a fluid tight seal once hardened or cured. The potting resin can comprise, for example, a multicomponent (resin and hardener component) thermosetting or UV-curable FDA grade resin, such as for example, silicone, urethane or epoxy, all of which can provide secure attachment of the fibers 40 within the housing 14, as well as insuring a fluid tight seal around the fibers 40 and against the interior surface 16.

The lumens of the fibers are in gas flow communication with the vent 24, thereby allowing gasses within the degassing chamber 18 to be exhausted, and allowing a vacuum to be applied to the chamber 18 through the vent 24.

A preferred membrane is that provided by Membrana, a division of Cellgard, LLC located in Charlotte, N.C. under the product name MicroModule 0.71X. The hollow fiber array is made of polypropylene with a typical membrane surface area of 392 cm$^2$ and is provided with a housing made of polycarbonate.

It is a desire that there be a vacuum at the vent 24 of about 25 to about 500 torr, and more preferably from about 50 to about 125 torr. The vacuum can be provided, as described in my aforementioned patent, by an external vacuum source. However, it is preferred that the device 10 be self-contained and provide its own vacuum, with a vacuum chamber 70 in the housing 14, the vacuum chamber 70 being in gas flow communication with the vent 24 for withdrawing gas from the inside of the lumens of the fibers 40 in the degassing chamber 18.

Inside the vacuum chamber 70 is a movable piston 74 that can move up and down, engaging the internal surface 16 of the housing 14. As the piston 74 moves upwardly, just as the piston of a syringe moves, it creates a vacuum at the vent 24 for withdrawing gas from the degassing chamber 18. The piston 74 is biased upwardly, such as by a biasing spring 76 attached at one end to the piston 74 and the other end to an upper internal surface of 78 of the housing 14. As gas bubbles are removed from the incoming liquid, the gas fills the region 80 of the vacuum chamber 70 below the piston 74, with the result that the piston 74 moves upwardly under the force of the biasing spring 76.

An indicator is provided to identify when enough gas has been removed from the incoming liquid that the piston no longer provides an effective vacuum. The indicator can be a visible mark 82 on the housing. This indicates that the device 10 needs to be replaced or adjusted For safety, an alert switch 84 can be provided on the housing 14. The alert switch 84 can be a toggle switch so that when the piston 74 reaches the toggle switch, the switch is activated and a perceptible alert is provided so that the staff knows it is time to change out the device 10 or adjust the device 10. The alert can be an alarm such as an audible beep or flashing lights, or an electronic signal to a nursing station, or any combination thereof. Rather than changing out the device, it can be adjusted to continue to produce an adequate vacuum, such as by aspirating gas from the region 80 below the piston ring.

Preferably the device 10 is provided with a vacuum connection 90 in the housing 14 for attachment to an external vacuum source where such a source is available. Thus, the device 10 can be used without an external vacuum source, or with an external vacuum source. The vacuum connection 90 is provided with a cap 92 for closing it.

The device of the present invention is utilized by installing the device in a liquid inlet line. The inlet port 20 is connected to an infusion line 12 system and the outlet port 22 is connected, preferably by means of quick connect fittings, to a line 94 for infusion into a patient. An external vacuum source can be connected to the optional vacuum outlet 90, or if an external vacuum source is not available, the external vacuum connection can be covered with the cap 92 and the vacuum created by the piston 74/spring 76 combination can be used for withdrawing the gas through the vacuum port 24 into the vacuum chamber 70.

Although the present invention has been described in considerable detail with reference to certain preferred version thereof, other versions are possible. For example, although in the drawings the device 10 is shown in a particular orientation with the vacuum chamber 70 above the degassing chamber 18, the device can be placed in any orientation. Directions are used in the application for convenience with respect to the orientation of the drawings. Similarly the device shown in the drawings has the degassing and vacuum chambers integrated in a single housing. Alternatively, they can be provided separately, where the vacuum chamber is provided as a separate add-on that can be attached to a vacuum port connector. In this alternate version of the invention, the Membrana membrane debubbler described above can be obtained from the manufacturer, and the vacuum chamber can be attached to the vacuum port of the Membrana device. Another example of a modification is to install a pressure indicator on the housing. Also the biasing means can be made adjustable for controlling the vacuum in a desired range. In addition, the fibers need not be oriented with their longitudinal axis at an angle of 90 degrees relative to the fluid flow through the degassing chamber, but can be at any angle, including generally aligned with the direction of fluid flow. Also not all fibers need to have their longitudinal axis in the same direction.

Therefore, the spirit and scope of the appended claims should not necessarily be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means step" clause as specified in 35 U.S.C. §112.

What is claimed is:

1. A device for removal of gas from a liquid being delivered to a patient through a medical fluid infusion line, the device comprising:
    a) a housing having an internal surface, an internal degassing chamber in the housing, a vacuum chamber in the housing, an inlet port for receiving liquid from the medical fluid infusion line for flow into the internal degassing chamber, an outlet port for discharging the liquid from the degassing chamber, and a vent in communication with the degassing chamber for passing gas from the degassing chamber to the vacuum chamber;
    b) a plurality of hollow fiber membranes in the internal degassing chamber for removing gas from the liquid, wherein removed gas is in gas flow communication with the vent; and
    c) a mechanical source of vacuum in the housing containing the hollow fiber membranes, the mechanical source of vacuum being movably mounted in the vacuum chamber and entirely in the housing and in gas flow communication with the vent for withdrawing gas from the internal degassing chamber to the vacuum chamber so that the device is self-contained and adapted for use without connection to an external source of vacuum,
    wherein the mechanical source of the vacuum comprises a piston having a length about equal to the distance between the inlet port and the outlet port, the piston being biased away from the vent by a spring.

2. The device of claim 1 wherein the vacuum at the vent is from about 25 ton to about 500 torr.

3. The device of claim 2 wherein the vacuum at the vent is from about 50 torr to about 125 torr.

4. The device of claim 1 comprising an indicator for indicating when the piston has moved to a warning position that the piston no longer provides an effective vacuum.

5. The device of claim 4 comprising an alert switch activatable by the piston for providing a perceptible alert that the piston no longer provides an effective vacuum, the alert switch being positioned that the alert switch is activated after the piston has moved to the warning position.

6. The device of claim 5 wherein the perceptible alert is selected from the group consisting of an audible beep, flashing lights, and an electric signal.

7. A method for removing gas from a liquid infused to an internal delivery site of an organism, the method comprising the steps of:
    a) selecting the device of claim 4; and
    b) introducing the liquid into the inlet port of the device; and
    c) replacing or adjusting the device after the piston moves to the warning position.

8. The device of claim 1 comprising an alert switch activatable by the piston for providing a perceptible alert to replace or adjust the device.

9. A method for removing gas from a liquid infused to an internal delivery site of an organism, the method comprising the steps of:
    a) selecting the device of claim 8;
    b) introducing the liquid into the inlet port of the device; and
    c) replacing the device when the perceptible alert is perceived.

10. A method for removing gas from a liquid infused to an internal delivery site of an organism, the method comprising the steps of:
    a) selecting the device of claim 1; and
    b) introducing the liquid into the inlet port of the device.

11. The device of claim 1 wherein each hollow fiber membrane has an external wall and an internal lumen and are substantially impervious to the liquid and are pervious to gas in the liquid, wherein the external wall of each hollow fiber membrane is in liquid flow communication with the inlet port but not in gas flow communication with the vent, and
    wherein the internal lumens of each hollow fiber membrane is in gas flow communication with the vent but not in liquid flow communication with the inlet port, so that gas in the liquid can pass through the external wall of each hollow fiber membrane without the liquid and be vented from the hollow fiber membranes through the vent.

12. The device of claim 1 wherein the housing has a vacuum connection in communication with the degassing chamber, wherein the vacuum connection can be attached to an external source of vacuum so the device can be used both with an external source of vacuum and without the external source of vacuum.

13. The device of claim 12 comprising a cap for optionally closing the vacuum connection.

14. A method for removing gas from a liquid being infused to an internal delivery site of an organism, the method comprising the steps of:
    a) selecting the device of claim 13, wherein if the cap is on the vacuum connection the cap is removed from the vacuum connection;
    b) connecting the vacuum connection to a vacuum source; and
    c) introducing the liquid into the inlet port of the device, wherein gas is removed from the liquid and sucked through the vacuum connection toward the vacuum source.

15. A device suitable for removal of gas from a liquid being delivered to a patient through a medical fluid infusion line, the device comprising:
    a) a housing having an internal surface, an internal degassing chamber in the housing, a vacuum chamber in the housing, an inlet port for receiving liquid from the medical fluid infusion line for flow into the internal degassing chamber, an outlet port for discharging the liquid from the degassing chamber, a vent in communication with the degassing chamber for passing gas from the degassing chamber to the vacuum chamber, and a vacuum connection in communication with the degassing chamber;
    b) a plurality of hollow fiber membranes in the internal degassing chamber for removing gas from the liquid, wherein removed gas is in gas flow communication with the vent and the vacuum connection; and c) a mechanical source of vacuum completely in the housing and comprising a piston movably mounted in the vacuum chamber and a spring biasing the piston away from the vent, the spring and piston being in gas flow communication with the vent for withdrawing gas from the internal degassing chamber so that the device is self-contained and adapted for use without connection to an external source of vacuum;

d) wherein the vacuum connection can be attached to the external source of vacuum so the device can be used both with the external source of vacuum and without the external source of vacuum; and e) a cap for optionally closing the vacuum connection.

* * * * *